United States Patent
Ortega Higueruelo et al.

(10) Patent No.: US 10,597,342 B2
(45) Date of Patent: Mar. 24, 2020

(54) METHOD FOR THE SYNTHESIS OF 9,10-BIS(CHLOROMETHYL)ANTHRACENE

(71) Applicant: UNIVERSIDAD DE CASTILLA LA MANCHA, Albacete (ES)

(72) Inventors: Francisco José Ortega Higueruelo, Albacete (ES); Fernando Langa De La Puente, Albacete (ES)

(73) Assignee: UNIVERSIDAD DE CASTILLA LA MANCHA, Albacete (ES)

( * ) Notice: Subject to any disclaimer, the term of this patent is extended or adjusted under 35 U.S.C. 154(b) by 0 days.

(21) Appl. No.: 16/575,035

(22) Filed: Sep. 18, 2019

(65) Prior Publication Data

US 2020/0010391 A1 Jan. 9, 2020

Related U.S. Application Data

(63) Continuation of application No. PCT/ES2018/070196, filed on Mar. 16, 2018.

(30) Foreign Application Priority Data

Mar. 29, 2017 (ES) .................... 201730460

(51) Int. Cl.
*C07C 17/32* (2006.01)
*C07C 22/04* (2006.01)
*C07C 17/00* (2006.01)
*C07C 25/18* (2006.01)

(52) U.S. Cl.
CPC .............. *C07C 17/32* (2013.01); *C07C 17/00* (2013.01); *C07C 22/04* (2013.01); *C07C 25/18* (2013.01)

(58) Field of Classification Search
CPC ......... C07C 17/32; C07C 22/04; C07C 17/00; C07C 25/18
See application file for complete search history.

(56) References Cited

U.S. PATENT DOCUMENTS 4,558,163 A 12/1985 Peake

FOREIGN PATENT DOCUMENTS

CN  102108041  *  6/2011 ............. C07C 25/18
CN  102108041 A  6/2011

OTHER PUBLICATIONS

International Search Report issued for corresponding International Patent Application No. PCT/ES2018/070196, dated Jun. 4, 2018, with an English translation.
A Kannan et al. "Synthesis, photophysical and electrochemical properties of a new class of fluorescent amidoanthracenophanes", RSC Advances (Royal Society of Chemistry), 2015, vol. 5, pp. 73951-73957, downloaded from [https://www.researchgate.net/publication/281147779_Synthesis_photophysical_and_elctrochemical_properties_of_a_new_class_of_fluorescent_amidoanthracenophanes/link/55e6c52408ae1696972e174a/download].

* cited by examiner

*Primary Examiner* — Jafar F Parsa
(74) *Attorney, Agent, or Firm* — Myers Wolin, LLC

(57) ABSTRACT

The invention relates to a method for the synthesis of 9,10-bis(chloromethyl) anthracene, comprising the mixing of the reagents, anthracene and 1,3,5-trioxane, a phase transfer catalyst selected from the group comprising quaternary ammonium salt and crown ether with hydrochloric acid and acetic acid.

3 Claims, 1 Drawing Sheet

METHOD FOR THE SYNTHESIS OF 9,10-BIS(CHLOROMETHYL)ANTHRACENE

CROSS REFERENCE TO RELATED APPLICATIONS

This application is a continuation application of International Application No. PCT/ES2018/070196, filed Mar. 16, 2018, which claims priority to Spanish Patent Application P201730460, filed Mar. 29, 2017, the contents of each of which are incorporated by reference herein.

FIELD OF THE INVENTION

The present invention relates to a method for the synthesis of 9,10-bis(chloromethyl)anthracene. The method involves the mixing of anthracene, 1,3,5-trioxane, the catalyst hexadecyltrimethylammonium bromide, hydrochloric acid and acetic acid. 9,10-bis(chloromethyl)anthracene is a compound used in specific recognition, electronic molecular machines, drug carriers and catalysts in organic synthesis, optical fluorescence, photodynamic therapy and optical data storage, microfabrication, precursor in the preparation of anthracene meso bi-substituted derivatives.

BACKGROUND OF THE INVENTION

The compound 9,10-bis(chloromethyl)anthracene

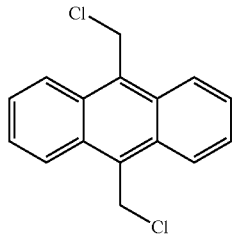

is a compound of high interest as an intermediate for chemical synthesis processes where the inclusion of an anthracene skeleton that is doubly substituted in the meso or benzylic position ($CH_2$ adjacent to the aromatic ring) is necessary.

Document J. Am. Chem. Soc. 1955, 77, 2845-2848 describes a chloromethylation method of anthracene as a versatile intermediate in obtaining other derivatives by means of displacement reactions, that is, from 9,10-bis(chloromethyl)anthracene to a wide range of available functionalisation. In summary, the synthetic method described in this document consists of passing a current of cool hydrogen chloride, continuously generated in situ, to a mixture of 1,4-dioxane, anthracene, p-formaldehyde and fuming hydrochloric acid. The crude reaction product is heated under reflux, maintaining the current of hydrogen chloride for several hours, after the interruption thereof, the reflux system continues for another 24 hours. After filtering and thorough washing to remove impurities, the compound is finally obtained in solid form with a fairly moderate yield of 67%. As can be seen, it is a rather laborious experiment with a yield that can be significantly improved.

Other synthetic methods have been described in the state of the art, such as that described in RSC Adv. 2015, 5, 73951-73957, where the synthesis is carried out in the presence of an organic solvent (dioxane) and at high temperatures (100° C.).

However, the inventors of the present application have found serious reproducibility problems in this method. When the inventors reproduced the method, they found that 9,10-bis(chloromethyl)anthracene is not obtained, as stated in the scientific article, despite having repeated this reaction several times, and being unsuccessful every time. Therefore, this synthesis route must be discarded.

9,10-bis(chloromethyl)anthracene can be acquired from different suppliers. On their website, Sigma-Aldrich classifies this product within a selection of "uncommon and unique chemical reagents", thus justifying its fairly high price. However, this compound is widely used in scientific work as a structural intermediate for anthracene, which is freely chemically derivatised, mainly seeking the occurrence of colorimetric and fluorescent optical properties.

Some applications of this compound have been published in the state of the art.

Document RSC Adv. 2015, 5, 73951-73957 describes this compound as a new photoactive cyclophanes skeleton with molecular rigidity for use in specific recognition, electronic molecular machines, drug carriers and catalysts in organic synthesis.

Document Chem. Mater. 2004, 16, 2783-2789 describes this compound as organic matter for application in optical fluorescence, photodynamic therapy and optical data storage and microfabrication through donor-bridge-acceptor compounds or donor-bridge-donor compounds.

This compound acts as a valuable precursor in the preparation of anthracene meso bi-substituted derivatives in positions 9 and 10, such as amines and the respective hydrochlorides thereof, amides, isocyanates, alcohols, esters, ethers, thiols, nitriles, acids and phosphonates.

DESCRIPTION OF THE INVENTION

In light of the state of the art, the problem consists of providing a method for the synthesis of 9,10-bis(chloromethyl)anthracene with a higher yield to that obtained with the methods of the state of the art.

The solution to this problem consists of providing the method described below, a much simpler scaling that those described to date and meeting the "green chemistry" principles as it uses a catalytic method and an aqueous reaction medium without the presence of organic solvents.

In a first aspect, the present invention provides a method for the synthesis of 9,10-bis(chloromethyl)anthracene, comprising the mixing of the reagents, anthracene and 1,3,5-trioxane, a phase transfer catalyst selected from the group comprising quarternary ammonium salt and crown ether with hydrochloric acid and acetic acid.

In the present specification, a "phase transfer catalyst" is the chemical species that makes possible and catalyses chemical reactions between two or more reagents situated in two or more phases, such that it enables a reactivity that, without the phase transfer catalyst, would not be possible. The mode of operation is based on the arrangement of the catalyst between the phases, enabling the physicochemical connection between the reagents that actively participate in the reaction.

Another embodiment is the method according to the first aspect of the invention, wherein the concentration of the phase transfer catalyst is between 1 and 5 mol %.

Another embodiment is the method according to the first aspect of the invention, wherein the concentration of hexadecyltrimethylammonium bromide is between 2 and 4 mol %.

Another embodiment is the method according to the first aspect of the invention, wherein the concentration of hexadecyltrimethylammonium bromide is between 2 and 3 mol %.

Another embodiment is the method according to the first aspect of the invention, wherein the molar ratio of 1,3,5-trioxane:anthracene is between 0.5 and 3.

Another embodiment is the method according to the first aspect of the invention, wherein the molar ratio of 1,3,5-trioxane:anthracene is between 1 and 2.

Another embodiment is the method according to the first aspect of the invention, comprising the following additional stages:

(c) filtering the mixture resulting from stage (b),
(d) washing with water and
(e) washing with ethanol.

The method according to the first aspect of the invention can be carried out at room temperature or heated to temperatures higher than room temperature.

The 9,10-bis(chloromethyl)anthracene compound appears very quickly, within a few minutes. This compound is present in less than 10 minutes from the start of the method according to the first aspect of the invention.

The method according to the first aspect of the invention has a series of advantages with respect to the methods described in the state of the art, which are:

- the absence of any organic solvent in the synthesis process, the medium used being exclusively aqueous, which entails preventing the need to treat the organic solvents;
- the absence of accessory gas supply currents to the process;
- the high reaction yield measured as the mass of the final purified product in solid state;
- not requiring high temperatures in the synthesis, since it is not necessary to reflux the solvent;
- not requiring further purification of the final product by crystallisation has had been the case;
- the excellent reproducibility of the method.

DESCRIPTION OF THE EMBODIMENTS

Reagents Used

Figure 1:
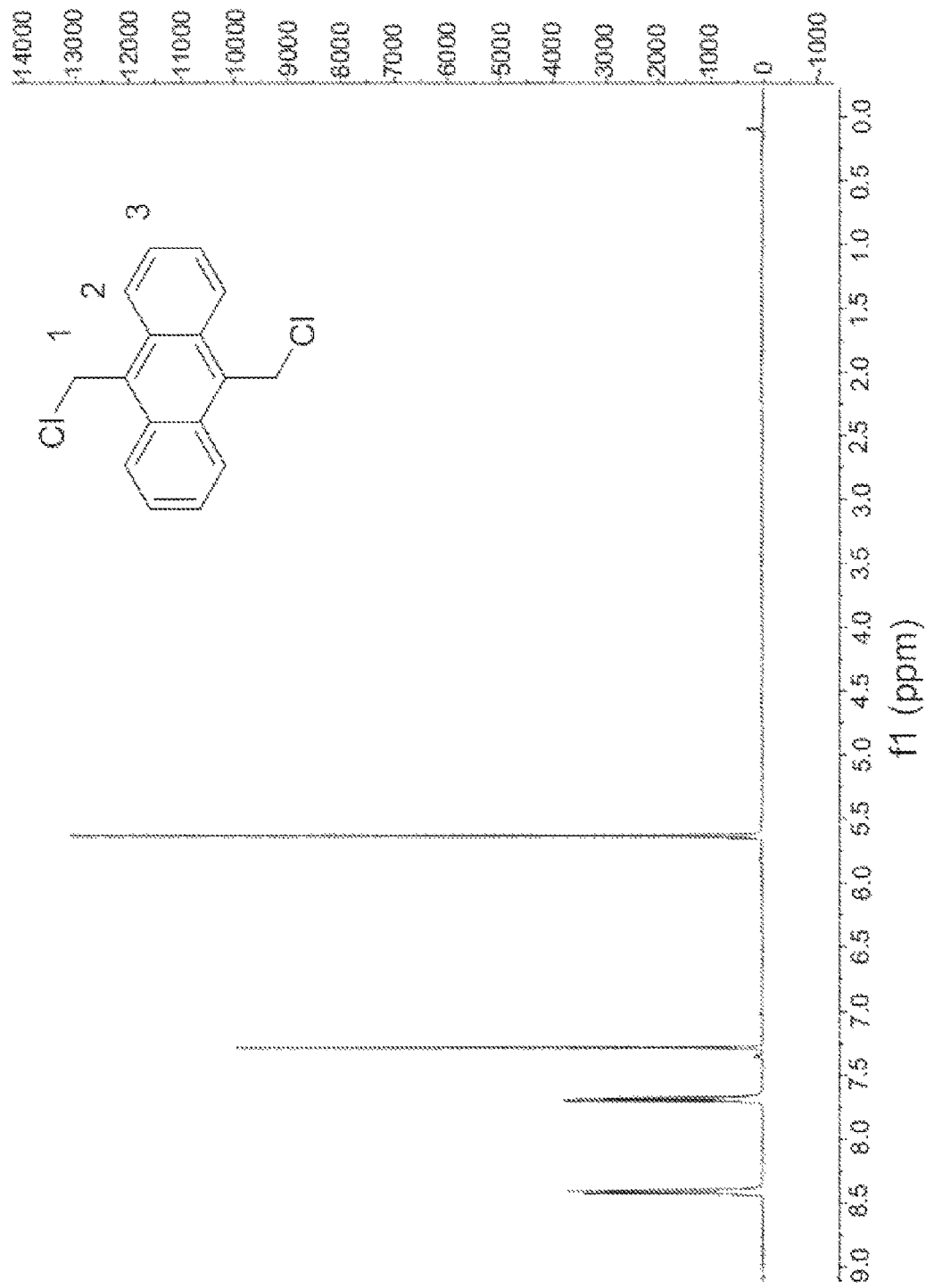
FIG. 1. 400 MHz proton NMR spectrum in deuterated chloroform and at room temperature of 9,10-bis(chloromethyl)anthracene.

The reagents used in the method for the synthesis were used based on the commercial compound without purification or enrichment thereof before the synthesis.

The reagents anthracene (Anthracene ReagentPlus®, 99%, commercial code 141062-25G, 56.00 €, Spain), acetic acid (Acetic acid ReagentPlus®, ≥99%, commercial code A-6283-1 L, 43.60 €, Spain) and 1,3,5-trioxane (1,3,5-trioxane, ≥99%, commercial code T81108-100G, 23.30 €, Spain) were acquired from Sigma-Aldrich. The hydrochloric acid (Hydrochloric acid reagent grade, 37%, 1 L, 28.23 €) was supplied by Scharlab. Lastly, the hexadecyltrimethylammonium bromide (Hexadecyltrimethylammonium bromide, ≥96%, commercial code 52370-100G, 32.00 €, Spain) is from Fluka.

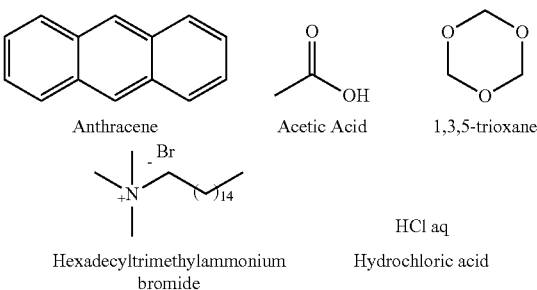

Method for the Synthesis of
9,10-bis(chloromethyl)anthracene

In general, the experimental method can be described as follows: the solid reagents (anthracene, 1,3,5-trioxane and hexadecyltrimethylammonium bromide as a catalyst) are placed in a round flask without an established order of priority. Firstly, the hydrochloric acid is added to the mixture, then the acetic acid, all at room temperature and under constant and vigorous stirring (1500 rpm). Then, the mixture is exposed to different temperatures in order for the reaction to take place during a specific period of time, wherein the medium becomes a yellow colour and has a powdery appearance, without dissolving the solid present. After a fixed reaction time, the content of the flask is filtered in order to collect the yellow precipitate and it is thoroughly washed with water to eliminate the remains of trioxane, catalyst and acid species present in the medium. As a final step, the obtained solid is washed with ethanol to remove the remains of water from the washing and it is left to stove dry at 70° C. for 2 hours until completely dry.

Several reaction protocols have been tested with different values for reaction temperature, time and excess of 1,3,5-trioxane as a source of formaldehyde with respect to the limiting amount of anthracene.

Examples 1-4 describe the different methods for the synthesis of 9,10-bis(chloromethyl)anthracene that were tested.

Example 1. Method for the Synthesis of
9,10-bis(chloromethyl)anthracene

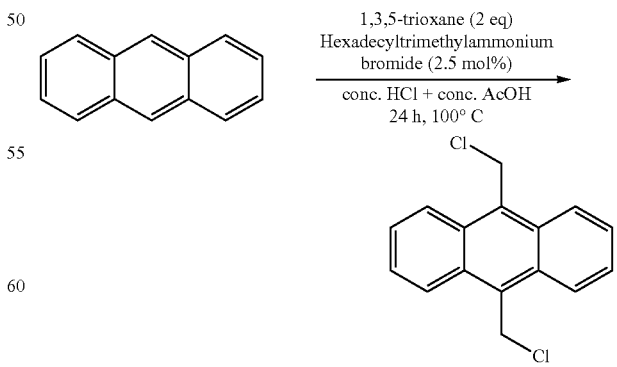

Description of Reagent Amounts Used:
Anthracene 500 mg, 2.8 mmol.
1,3,5-trioxane 504 mg, 2 eq (5.6 mmol).

Hexadecyltrimethylammonium bromide 25 mg, 0.07 mmol (2.5 mol %)
Hydrochloric acid 37% 10 ml
Acetic acid 99% 2.5 ml
Reaction yield: 89%

Example 2. Method for the Synthesis of 9,10-bis(chloromethyl)anthracene

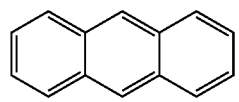

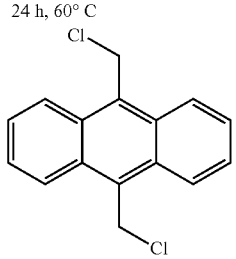

Description of Reagent Amounts Used:
Anthracene 500 mg, 2.8 mmol.
1,3,5-trioxane 504 mg, 2 eq (5.6 mmol).
Molar ratio 1,3,5-trioxane:anthracene: 2
Hexadecyltrimethylammonium bromide 25 mg, 0.07 mmol (2.5 mol %)
Hydrochloric acid 37% 10 ml
Acetic acid 99% 2.5 ml
Reaction yield: 96%.

Example 3. Method for the Synthesis of 9,10-bis(chloromethyl)anthracene

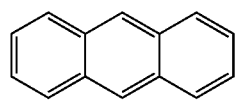

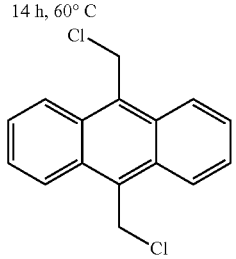

Description of Reagent Amounts Used:
Anthracene 500 mg, 2.8 mmol.
1,3,5-trioxane 504 mg, 2 eq (5.6 mmol).
Molar ratio 1,3,5-trioxane:anthracene: 2
Hexadecyltrimethylammonium bromide 25 mg, 0.07 mmol (2.5 mol %)
Hydrochloric acid 37% 10 mi
Acetic acid 99% 2.5 mi
Reaction yield: 93%.

Example 4. Method for the Synthesis of 9,10-bis(chloromethyl)anthracene

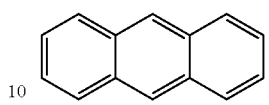

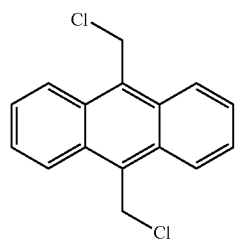 [SMILES: ClCc1c2ccccc2c(CCl)c2ccccc12]

Description of reagent amounts used: Anthracene 500 mg, 2.8 mmol.
1,3,5-trioxane 504 mg, 1 eq (2.8 mmol).
Molar ratio 1,3,5-trioxane:anthracene: 1
Hexadecyltrimethylammonium bromide 25 mg, 0.07 mmol (2.5 mol %)
Hydrochloric acid 37% 10 ml
Acetic acid 99% 2.5 ml
Reaction yield: 97% of solid that does not correspond through NMR analysis with pure product, but rather there is presence of unreacted anthracene.

Below, Table 1 shows an informative table summarising the above results based on the variables.

TABLE 1

| Variables | Example 1 | Example 2 | Example 3 | Example 4 | Example 5 |
|---|---|---|---|---|---|
| Time (h) | 24 | 24 | 14 | 24 | 24 |
| Temperature (° C.) | 100 | 60 | 60 | 60 | 25 |
| Molar ratio 1,3,5-trioxane:anthracene | 2 | 2 | 2 | 2 | 1 |
| Yield by weight (%) | 89 | 96 | 93 | 97 | 74 |

The 9,10-bis(chloromethyl)anthracene synthesised in Examples 1-4 was characterised through proton nuclear magnetic resonance (NMR) experiments in a Bruker 400 MHz NMR, carrying out the measurements at room temperature and using deuterated chloroform ($CDCl_3$) as a solvent in the analysis.

FIG. 1 shows the 400 MHz proton NMR spectrum in deuterated chloroform and at room temperature. This spectrum is identical for the compound obtained in Examples 1-4. The spectrum coincides with the spectrum described in the state of the art ($\delta$H400 MHz, $CDCl_3$: 5.77 ppm, singlet, 4H; 7.74-7.77 ppm, multiplet, 4H; 8.53-8.55 ppm, multiplet, 4H).

Example 5. Method for the Synthesis of 9,10-bis(chloromethyl)anthracene

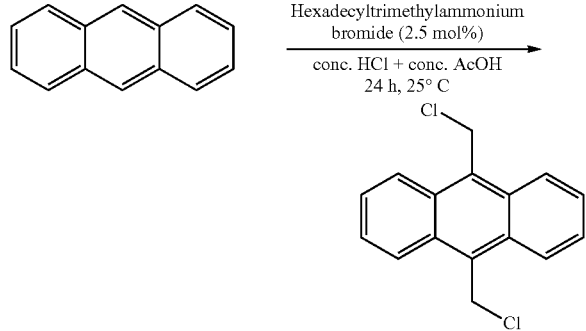

Description of Reagent Amounts Used:
Anthracene 500 mg, 2.8 mmol.
1,3,5-trioxane 504 mg, 2 eq (5.6 mmol).
Molar ratio 1,3,5-trioxane:anthracene: 2
Hexadecyltrimethylammonium bromide 25 mg, 0.07 mmol (2.5 mol %)
Hydrochloric acid 37% 10 ml
Acetic acid 99% 2.5 mi Reaction yield: 74% of solid.

Example 6. Method for the Synthesis of 9,10-bis(chloromethyl)anthracene

In this example, the following phase transfer catalysts were used:
Tetrabutylammonium bromide
Tetrabutylammonium fluoride
Tetrabutylammonium nitrate
Tetrabutylammonium hexafluorophosphate
Tetrabutylammonium perchlorate
Benzyl trimethylammonium chloride
4-carboxybenzyl-18-crown-6 (1,4,7,10,13,16-Hexaoxacyclooctadecane 1,4,7,10,13,16-Hexaoxacyclooctadecane) crown ether 18-crown-6 (carboxylic acid 18-2,3,5,6,8,9,11,12,14,15-decahydrobenzo[b][1,4,7,10,13,16]hexaoxacyclooctadecane 2,3,5,6,8,9,11,12,14,15-decahydrobenzo[b][1,4,7,10,13,16]hexaoxacyclooctadecane-18-carboxylic acid) crown ether Table 2 shows the reaction parameters and yield obtained in the experiments of this example:

TABLE 2

| Phase transfer catalyst used | Reaction time (h)/ temperature (° C.) | Yield by weight of pure product (%) |
| --- | --- | --- |
| Tetrabutylammonium bromide | 24/60 | 83 |
| Tetrabutylammonium fluoride | 24/60 | 80 |
| Tetrabutylammonium nitrate | 24/60 | 71 |
| Tetrabutylammonium hexafluorophosphate | 24/60 | 70 |
| Tetrabutylammonium perchlorate | 24/60 | 75 |
| Benzyl trimethylammonium chloride | 24/60 | 70 |
| 4-carboxybenzyl-18-crown-6 crown ether | 24/60 | 67 |
| 18-crown-6 crown ether | 24/60 | 63 |

What is claimed is:

1. A method for the synthesis of 9,10-bis(chloromethyl) anthracene comprising: mixing the reagents containing anthracene and 1,3,5-trioxane, a phase transfer catalyst selected from the group consisting of quarternary ammonium salt and crown ether with hydrochloric acid and acetic acid.

2. The method according to claim 1, characterised in that the concentration of the phase transfer catalyst is between 1 and 5 mol %.

3. The method according to claim 1 or 2, characterised in that the molar ratio of 1,3,5-trioxane:anthracene is between 0.5 and 3.

* * * * *